United States Patent [19]
LaCourse et al.

[11] Patent Number: 5,002,065
[45] Date of Patent: Mar. 26, 1991

[54] VIBRATORY SCREENING OR DIAGNOSTIC SYSTEMS

[75] Inventors: John R. LaCourse, Lee, N.H.; Thomas F. McCoy, Yarmouth, Me.

[73] Assignee: Link Performance and Recovery Systems, Portland, Me.

[21] Appl. No.: 183,901

[22] Filed: Apr. 20, 1988

[51] Int. Cl.$^5$ ............................................. A61B 15/00
[52] U.S. Cl. .................... 128/739; 128/744; 73/663
[58] Field of Search .............. 128/739, 740, 744, 774, 128/782; 73/662, 663

[56] References Cited

U.S. PATENT DOCUMENTS 4,175,546 11/1979 Goldblatt et al. .................. 128/739
4,641,661 2/1987 Kalarickal ........................... 128/744

OTHER PUBLICATIONS

Lundborg et al., "Digital Vibrogram: A New Diagnostic Tool for Sensory Testing in Compression Neuropathy", *Journal of Hand Surgery*, vol. 11A, No. 5, pp. 693–699, Sep. 1986.
Borg et al., "Increase of Vibration Threshold during Wrist Flexion in Patients with Carpal Tunnel Syndrome", *Pain*, 26, pp. 211–219, 1986.
Hansford et al., "Blood Flow Changes at the Wrist in Manual Workers after Operative Interventions", *Journal of Hand Surgery*, vol. 11A, No. 4, pp. 503–508, Jul. 1986.

*Primary Examiner*—Randall L. Green
*Assistant Examiner*—Randy Shay
*Attorney, Agent, or Firm*—Robert Shaw

[57] ABSTRACT

A method of (and apparatus for) diagnosing a patient to measure sensory disturbances of the patient that includes the steps of applying normalized vibrator forces to a body portion or part (e.g., the finger) of the patient; automatically effecting discrete, but variable, vibrations of the body portion over a wide range of frequencies and at various vibratory amplitude levels at each vibration frequency; and noting the onset of sensory perception by the patient on an up-cycle at each vibration frequency and correlating the information, so derived, with the physical condition of the body portion or part. The method contemplates, once the onset of vibratory perception is achieved, in an up-cycle, decreasing the amplitude of vibration at each vibration frequency until the patient ceases or fails to sense the vibration and, in part, correlating the lower level of sensory perception to the condition of the body portion or part.

15 Claims, 3 Drawing Sheets

VIBRATORY SCREENING OR DIAGNOSTIC SYSTEMS

FIELD OF THE INVENTION

The present invention relates to vibratory screening or diagnostic tools that may be used, for example, to measure sensory disturbances such as carpal tunnel syndrome (CTS) and to systems that include such tools.

DESCRIPTION OF RELATED ART

By way of background, attention is called to two journal articles: "Increase of Vibration Threshold During Wrist Flexion in Patients With Carpal Tunnel Syndrome," Borg et al., *Pain* at p. 211 (1986); "Digital Vibrogram: A New Diagnostic Tool for Sensory Testing in Compression Neuropathy," Lundborg et al., *The Journal of Hand Surgery*, at p. 693 (1986). In the references of these two articles there are further articles noted later herein: Dellon (1980); Gelberman (1980); Moberg (1966); Gelberman et al. (1983).

Muscles, nerves, tendons, and joints are all susceptible to fatigue when repetitive motion is required. Symptoms include numbness, aching, inflammation, and loss of skin color. One area of particular concern—and the disturbance emphasized herein—is the carpal tunnel, a section of the wrist through which a number of tendons move in their sheaths. Twisting, hyperextension and related conditions can cause a pinching of the tendons and/or nerves associated with this congested area of the hand and wrist. This is commonly referred to as the carpal tunnel syndrome.

Vascular injury can occur when the walls of the blood vessels in the fingers and elsewhere become thicker and constrict, thereby reducing blood flow. When passage becomes blocked and blood fails to flow through the vessels, the skin may turn pale. This is known as white fingers, Raynauds phenomenon, VWF (vibration induced white fingers) or TVD (traumatic vasospastic disease).

Nerve injury can also be induced by excessive vibration. It is often exhibited by an inability to identify two adjacent pressure points acting on the skin of the finger as two separate points and not just one. The sensory threshold is increased for fingers that have been injured by vibration.

High vibration amplitudes (at low frequencies) combined with high feed forces can cause wear on the surfaces of the joints. Likewise, impact can cause microfractures in skeletal bones, thus interfering with the supply of nutrients to the joints and causing pain.

All of the above injuries can be prevented if a noninvasive device existed that could predict the injury to the hands before irreversible damage occurs. In this regard it is necessary to detect early sensory changes in compression neuropathy.

By way of historical review, it is to be noted that Dellon (1980) and Gelberman (1980) found that an increase in the perception threshold for vibration stimuli of the long finger at 256 hertz is the earliest detectable objective sign in patients with CTS. Before this body of work, the two-point discrimination test (2PD) was used as a standardized test for assessing sensory improvement, but in compression neuropathy, changes in two-point discrimination only occurs in advanced nerve lesions (Moberg, 58, 62, 66). Gelberman et al. (1983) used a biothesiometer allowing assessment of perception threshold for vibration with a specific frequency (125 or 256 hertz). Lundborg et al. (1986) hypothesized that to detect early sensory changes in compression neuropathy, assessment of vibration sense of the hand was useful; but an analysis within only one fixed frequency and receptor system, respectively, gave a limited amount of information. Therefore, Lundborg et al. (1986) built an instrument, actually a modified Bekesy audiometer, for use in analyses of vibrotactile sensibility of the hand at frequencies ranging from eight to 500 hertz. They found that changes in the shape of a plot of perception threshold vs. frequency were related to the patients' subjective symptoms.

However, the above Lundborg et al. system appears not to have the necessary interactive measurement circuits to provide a diagnosis. Recent research by the present inventors suggest that six different measurements are required to effect the proper analysis. They are: (1) a plot of the perception threshold of the long finger (of a patient) vs. frequency (8–800 Hz); (2) force on the pulp of the long finger (other fingers or other body parts may be tested) by a vibratory stimulator; (3) uniform pressure of the entire hand of the patient on a vibrotactal measurement platform; (4) angle of the wrist of the patient; (5) finger tip temperature of the long (or other) finger; and (6) the PPG (i.e., pulsed wave graph or monitor). The Lundborg et al. (1986) system measures only (1).

OBJECTIVES

Accordingly, it is a principal objective of the present invention to provide a screening or diagnostic system to measure the extent of sensory disturbances in neuropathies and/or any response to treatment of any such sensory disturbances.

Another objective is to provide a system to measure early occurrence of carpal tunnel syndrome.

These and still further objectives are addressed herein.

SUMMARY OF THE INVENTION

The foregoing objectives are attained, generally, in a system (or method) to sense a body pressure-sensitivity phenomenon of a patient or pressure-related disorder of that patient, that includes a vibratory stimulator to apply controlled and compensated vibratory force to a finger (or other body portion) of the patient; a drive mechanism connected to effect vibration of the vibratory stimulator and operable automatically to effect discrete, but variable, vibrations at many frequencies over a wide range of frequencies and at variable amplitude levels at each vibration frequency; and a response mechanism which permits the patient to record the onset of sensing by the patient of vibrations (that is, the smallest amplitude of vibration sensed) at each discrete vibration frequency. In a preferred embodiment, once vibrations are noted (the onset of sensing) in an upcycle, i.e., a condition of increasing vibration amplitudes, the vibrations are then decreased, i.e., a downcycle, until no longer sensed, and that loss of vibration sensing is noted.

BRIEF DESCRIPTION OF THE DRAWINGS

The invention is hereinafter discussed with reference to the accompanying drawing in which.

DESCRIPTION OF THE PREFERRED EMBODIMENTS

Figure 1:
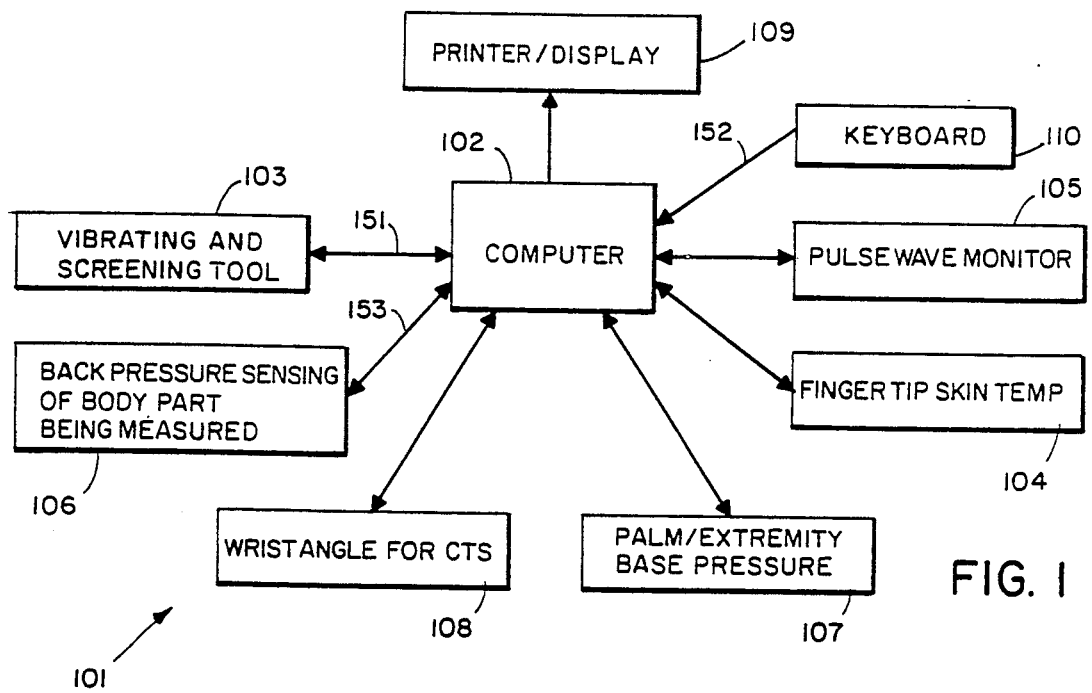
FIG. 1 is a diagrammatic representation of a system to sense a body pressure-sensitivity phenomenon or the like, that includes a vibratory tool, a computer, and a back-pressure monitor.

Turning first to FIG. 1, there is shown a system 101 to sense a body pressure phenomenon of a patient and/or a pressure-related disorder of the patient. The system 101 includes a computer 102, a printer/display 109, a vibratory screening and diagnostic tool 103, a fingertip skin temperature sensor 104, a pulse wave monitor (PPG) 105, a back-pressure monitor 106 of the measured body part, a base pressure sensor 107 and an extremity angle sensor for CTS measurement 108, and a keyboard 110. The units 103, 104, 105, 106, 107, 108, and 110 provide inputs to the computer 102 which provides control and data inputs to each of the units; thus, the double arrows. For present purposes the tool 103 is considered to have the electrical and mechanical structures shown at 103 in FIG. 2, as later discussed, and later figures.

Figure 5:
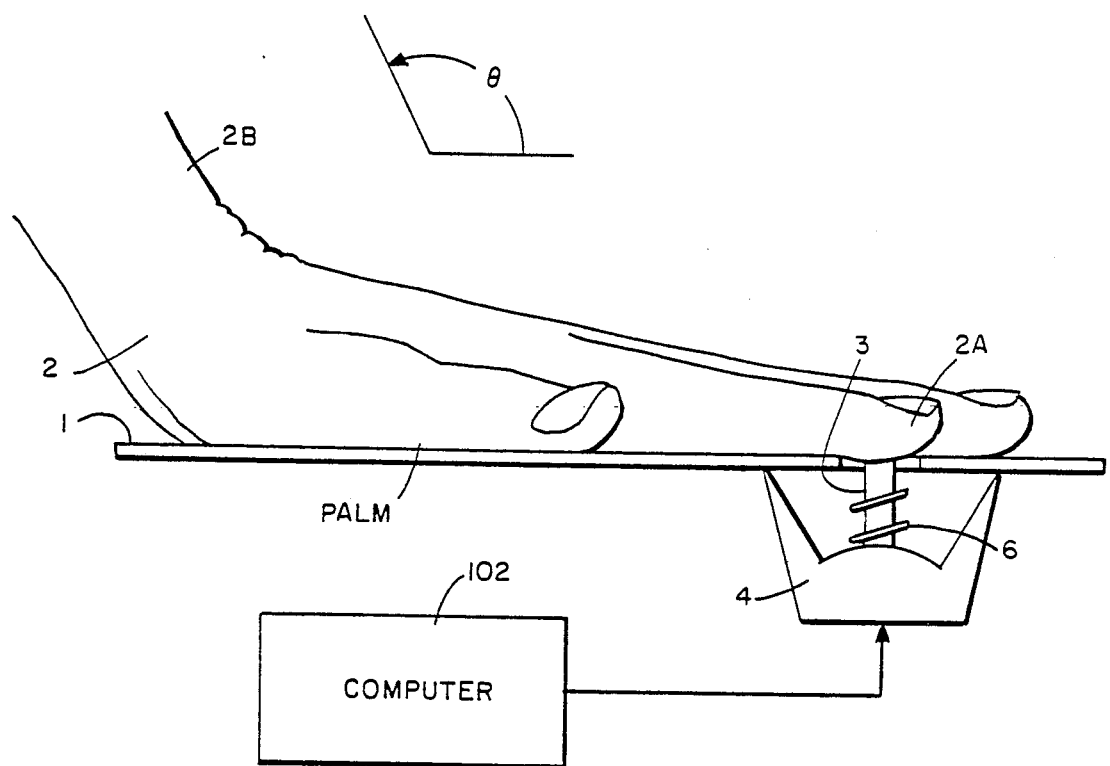
FIG. 5 is a side-view schematic diagram of portions of a vibratory tool and the hand of a patient properly placed for testing.
Figure 6:
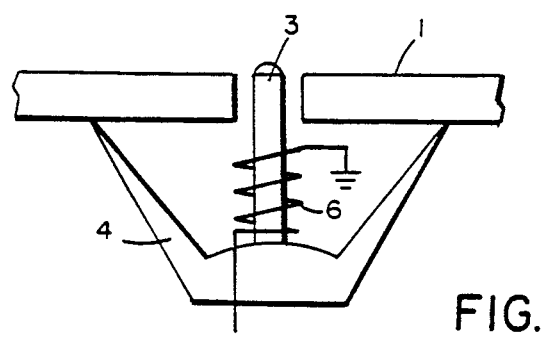
FIG. 6 is a more detailed side view schematic diagram showing portions of the vibratory tool and back-pressure monitor of FIG. 1, i.e., the electromagnetic vibration amplitude circuit herein.

The tool 103 includes a test surface 1 in FIGS. 5 and 6 to receive the hand 2 of a patient. A vibratory mechanism or probe 3 (that is, the core of a linear, variable, differential transformer) applies a vibratory force to the tip of a finger (labeled 2A in FIG. 5), or other body portion or part of the patient. The pulp of the tip 2A of the finger of the patient extends downward through a hole (or opening) 1A in the test surface 1; the probe 3 (FIG. 6) extends upward into the hole (or opening) 1A to apply an upward force on the pulp of the fingertip 2A. A probe drive functions to provide discrete, but variable, and compensated, vibrations at vibration frequency outputs from the vibratory probe over a wide range of frequencies (e.g., eight to 800 hertz). The probe drive is described below, but, for now, it includes a high-compliance speaker 4 (which may be replaced by a piezoelectric or other driver) and most of the apparatus to the left of the speaker 4 in FIG. 2 (e.g., a function generator 10, timer 11 and amplifier 7). The probe drive is such that the output of the probe 3 is linearized (i.e., the computer 102 on the basis of the feedback information from the back-pressure monitor 106 compensates for differences in force by individual patients upon the probe 3 so that, so far as the system 101 is concerned, each patient applies the same down pressure on the probe 3 over the entire frequency range). An electromagnetic vibration amplitude measurement coil 6 in FIG. 6 is used to determine vibration amplitude and also to determine back pressure on the probe tip 3 (an accelerometer may be used for this purpose). The coil 6 is part of the circuit in the back-pressure sensor of the body part being measured, that is, the block 106 in FIG. 1. The circuit 106 interacts with the computer connection 151C in FIG. 2 which is labeled 153 in FIG. 1) to maintain linearity in the system. (For each vibration amplitude setting the throw would be the same at all frequencies.)

Thus, the probe 3 may be driven at some low frequency, say eight hertz, and at an amplitude below that at which the patient can sense. The amplitude of vibration is increased (i.e., an up-cycle) until it is sensed by the patient, the onset of sensing. At that juncture the patient inputs at 5A in FIG. 2 a control signal to close an analog switch 5 to record the onset of sensing of the probe vibrations at the frequency being checked, here eight hertz. (The threshold is sensed several times in order to establish a zone of sensitivity.) A signal is sent to the computer 102 which is orchestrating the test and the frequency of vibration is increased from some lower value to some new, higher value, $f_1, f_2, f_3 \ldots f_n$, and the operation is repeated. In this way the onset of incipient level of sensed vibration at each frequency, $f_1, f_2, \ldots f_n$, is obtained and from this information the body pressure or pressure-related disorder of the patient can be learned or inferred. Both the up-cycle onset of vibration sensing and the down-cycle loss of sensed vibration provide data for body-function evaluation. Of great interest is carpal tunnel syndrome whose early stages are important to note in the context of treatment.

It is of some importance to note, as suggested above, that the threshold or onset of sensing by the patient to an increasing amplitude of vibration (an up-cycle) at each individual vibration frequency of a plurality of vibration frequencies over a range is important for diagnosis purposes. It is also important to note once the onset of vibration is established on the up-cycle, that the lower level of vibration, on the down-cycle, at which sensing of those vibrations is lost, is also important. For, once vibration sensitivity is established in a patient, it has been found for present purposes that the acoustic vibrational level can be reduced and yet the perception of vibration remains with the patient. There is a residual retention. The level of vibration amplitude—after the onset of vibration is noted (e.g., by depressing the switch 5)—is reduced to a lower level (the down-cycle) at which sensing ceases. This lowered level is noted by the patient by releasing the switch 5. Thus, according to this aspect of the invention, the onset of vibration sensing is noted by the patient depressing the switch 5 at each frequency $f_1, f_2 \ldots$ and the loss of sensing, as the vibrating amplitude is decreased is noted by the patient by releasing the switch 5. Both values are important for present purposes.

It is indicated above to be important that the fingertip 2A present about the same downward pressure onto the probe 3 in FIG. 5. For this and other reasons the arm 2B in FIG. 5 of the patient is oriented at an outside obtuse angle $\theta$ in FIG. 5 to the hand 2.

Figure 2:
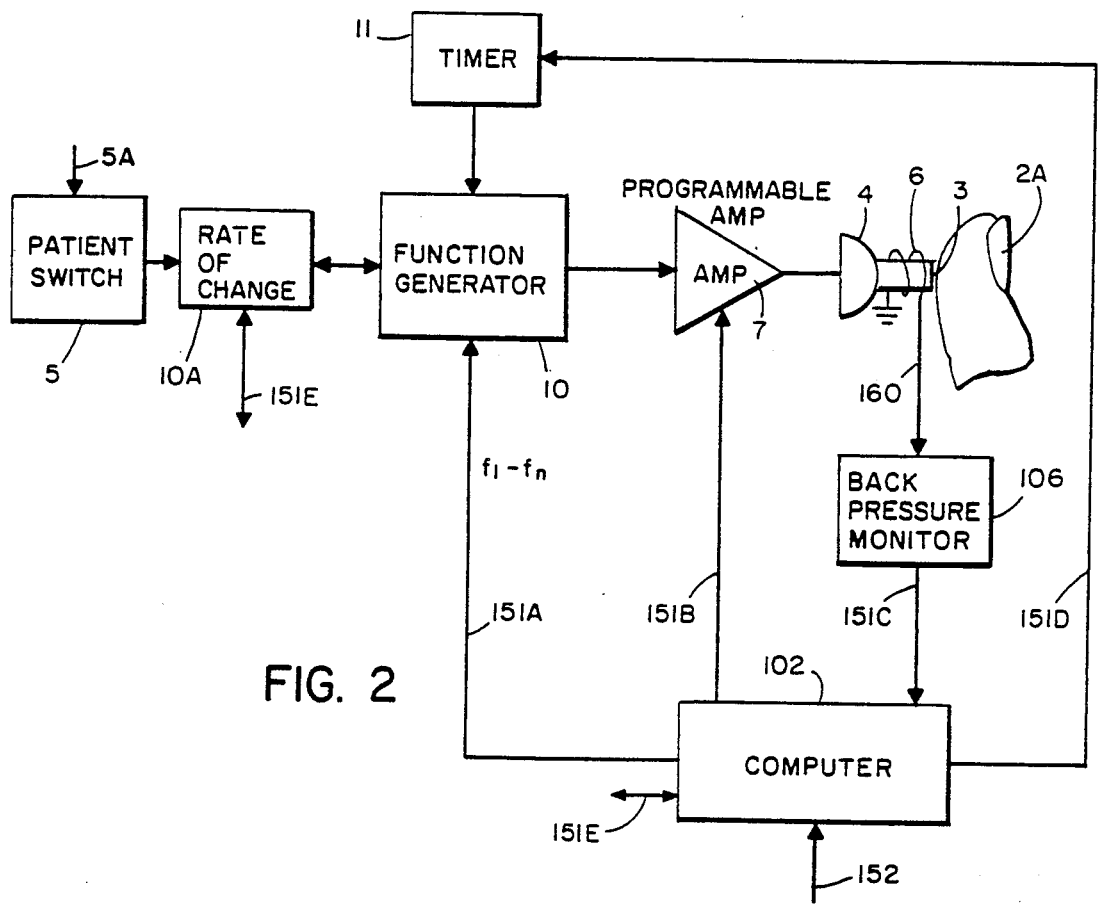
FIG. 2 is a diagrammatic representation showing in some detail the vibratory tool and the back-pressure monitor.

The patient is instructed to press the button 5A in FIG. 2 of the hand switch 5 when the vibrations of the probe 3 are first felt, thus causing an automatic attenuator to decrease the intensity (amplitude) and to release the button when the vibrations can no longer be felt. In this way the patients regulate the intensity (amplitude) of the vibrations, thereby tracking their threshold level.

Since the frequency of the stimuli is automatically changed through the frequency range from eight hertz to 800 hertz, the perception threshold within this frequency range can be recorded. As noted above, simultaneously real PPG data can be seen at 109. A readout at 109 can also show pulse rate and skin temperature, finger back pressure, base pressure, and wrist angle.

The main elements of the tool 103 are the high compliance speaker 4 driven by an amplifier 7 in FIG. 2. A magnetic post 3 is mounted/glued to the top of the speaker cone 4. The amplifier 7 linearizes the response of the system so that each individual is allowed to sense the same vibration at each frequency. The rest of the system consists of a function generator chip 10 in FIG. 2, a counter/timer 11, the analog switch 5, and a few bias amplifiers. A graphical printer 109 displays vibratory information in plot form as well as table form. The label 10A in FIG. 2 designates a circuit which controls the rate of rise and fall for the onset of vibration amplitude and the reduction in the amplitude.

The probe 3, then, is vibrated at frequencies $f_1 \ldots f_n$, e.g., 8 ... 800 hertz. At each frequency 8, 16 ... the probe starts with a force on the fingertip of zero (no initial contact); the computer 102 through the circuit 103 (see connection 151 in FIG. 1) increases the amplitude of vibration to a value at which the patient senses the vibration. Typically a cycle at each frequency is ten seconds. Each set of vibrations, it will be understood, is about an average value at each amplitude level. Taking 8 hertz as an example, the computer 102 may cause the probe 3 to vibrate in an up-cycle at level L, for one second or eight vibrations, at level $L_2$ for one second ... until level $L_n$ at which the vibrational force is sensed by the patient. At that juncture the patient closes the switch 5 and the computer systematically causes the vibratory pressure to decrease in a down-cycle. Meanwhile the patient keeps the switch 5 closed, until the sensing of vibration is lost; the switch 5 is then opened, beginning another up-cycle. Typically, there may be three up-cycles and three down-cycles at 8 hertz. The computer then repeats the process at 16 hertz, and so forth, up to, say, 800 hertz, but usually less. The number of frequencies $f_1, f_2 \ldots$ and the duration of each frequency are controlled and controllable by the computer 102.

Figure 3:
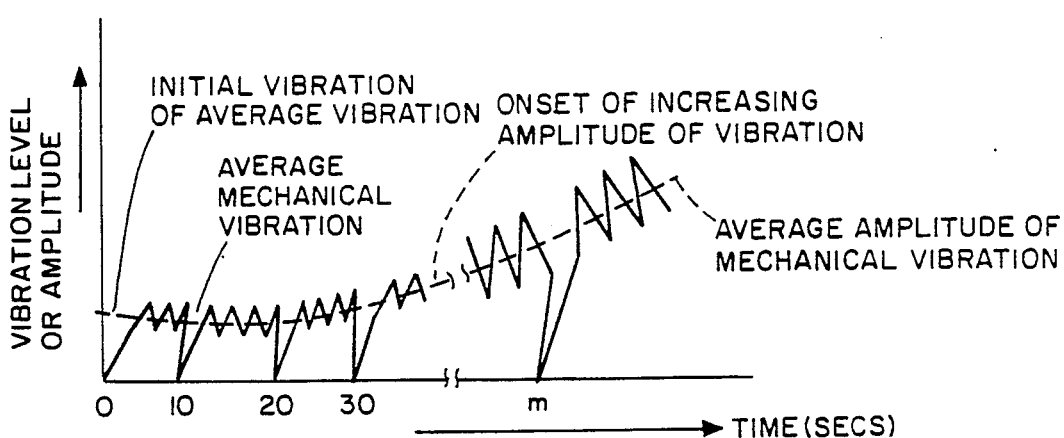
FIG. 3 is a graphical representation showing sensitivity of a normal patient to vibration of the vibratory tool of a body portion at discrete vibration frequencies over a range of frequencies.

It will be understood by workers in this art that the vibrations represented by the graph in FIG. 3 do not, then, proceed immediately from zero amplitude to the vibration amplitude at the onset of sensing, as shown, but, rather, there are intermediate vibrations, undetected by the patient. The graph shows only the detected vibration level at each frequency of the range of frequencies, for this is what is important, as is the average trend, as denoted in FIG. 4, of amplitude between the upper vibration level (on the up-cycle) and the lower vibration level (on the down-cycle) at each frequency.

Figure 4:
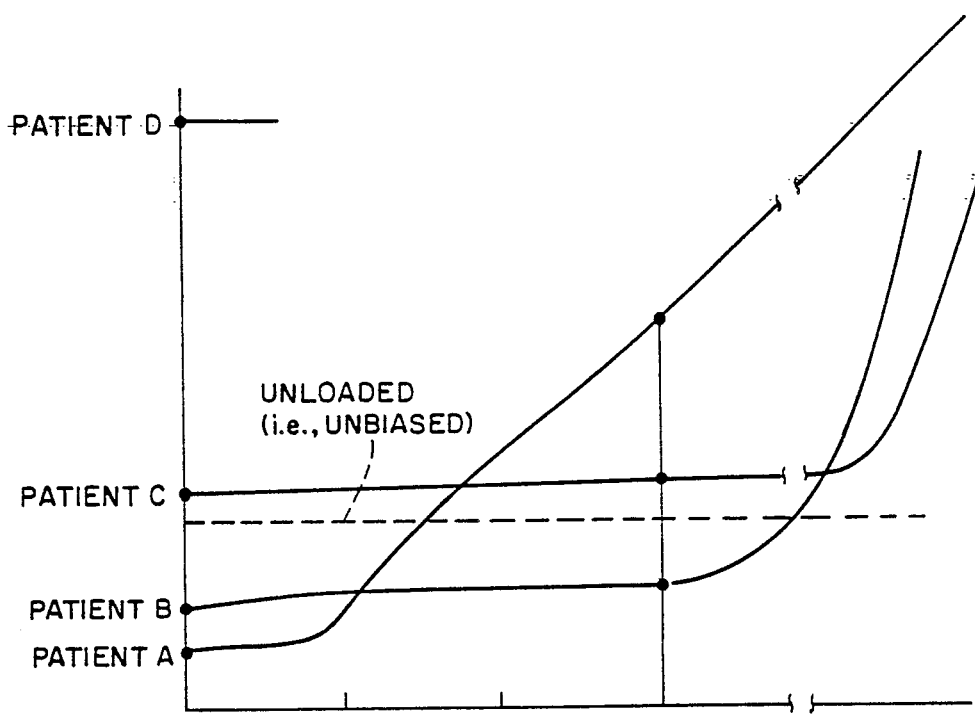
FIG. 4 is an exemplary graphical representation of perceived thresholds of perception for diseased and nondiseased patients with respect to body parts (e.g., carpal tunnel syndrome)

FIG. 4 shows how perceived thresholds can be used to diagnose diseased or non-diseased patients, such as carpal tunnel syndrome. Patient C senses a wider range of frequencies at a constant vibration amplitude than does patient A. Patient C is non-diseased; Patient A is diseased.

Figure 7:
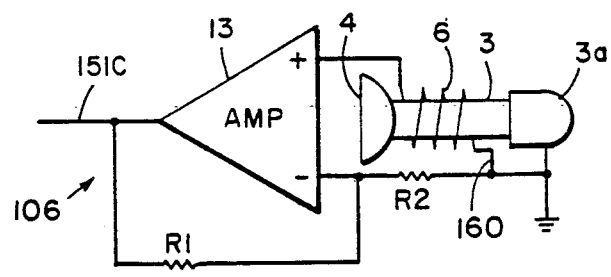
FIG. 7 is a schematic representation at the back-pressure monitor of FIG. 1.

Turning to the back pressure circuit 106 in FIGS. 1 and 7, it includes a programmable amplifier 13 and resistors $R_1$ and $R_2$. Its function is to compensate for mechanical bias applied to the end 3A of the probe 3 (FIG. 7) by a patient: patients will apply forces upon the probe 3 that vary from patient to patient and, as a function of time, even with the same patient. In the context of this specification, the circuit 106 includes the probe 3 and the coil 6. In the context of this explanation, feedback signals are applied at 160 from the coil 6 to the remaining circuitry in the circuit 106 and to the computer 102 (connection 151C). The circuit 106, on the basis of these feedback signals, compensates for the bias applied to the probe 3 by the patient to ensure that amplitude of vibration by the probe 3 to the finger tip 2A is the same for each patient as the vibrator tool 103 scans the frequencies $f_1 \ldots f_n$. The term "compensate" and variations thereof, as used herein, means compensation with respect to vibrations of the amplitude of the probe 3 at each frequency $f_1 \ldots$ to take into consideration, or compensate for, bias forces above or below some expected or average force by the patient.

A few matters touched on above are included in this paragraph. The computer 102 controls administration of the probe 3 to the patient and analysis of information received from the response recording devices 106, 107, 108, and the keyboard 110 (along connection 152, FIG. 1) provide feedback and other information to the computer 102. The feedback and other signals representing temperature (from the sensor 104) and the pulse wave monitor (PPG) 105 are used by the computer which is programmed to recalibrate and compensate respectively for temperatures of the fingertip that vary from an established standard and any functional vascular disorder of the patient. This latter technology is discussed at pp. 427 et seq. under the heading Photoplethysmography in Medical Instrumentation (Webster).

The connections 151A, 151B, 151D and 151E from the computer 102 are respectively to the function generator 10 (FIG. 2) to generate frequencies $f_1$-$f_n$, the amplifier 7 to amplify the signal out of the function generator 10 to drive the speaker 4, the timer 11 to control the timing of the sequence of test steps and the rate of change circuit 10A to control the rate at which vibration amplitude increases (or decreases) from some rate to a next different rate; the feedback signal at 151C to the computer 102 to provide information to enable the computer to provide compensation for back pressure.

The foregoing and further modifications of the invention will occur to persons skilled in the art and all such modifications are deemed to be within the scope of the invention as defined by the appended claims.

What is claimed is:

1. A vibratory screening or diagnostic system that comprises:

a test surface to receive the hand of a patient;

a vibratory probe operably associated with said test surface to apply vibratory force at a range of amplitudes and a range of frequencies to the tip of a finger of the patient;

a probe drive, means for providing compensated discrete, but variable amplitude, vibration frequency outputs from the vibratory probe over a wide range of test frequencies, the amplitude of vibration at each discrete frequency being varied throughout a range of amplitudes from some low value which is increased to the onset of incipient sensed amplitude of vibration;

means coupled to the vibratory probe for controlling said vibratory force to compensate for varying bias finger force onto the vibratory probe to permit application of a known vibratory force to said finger a response indicating device means for enabling the patient to indicate the force corresponding to onset and loss of sensed vibration at each test frequency.

2. A vibratory screening or diagnostic system according to claim 1, including means for reducing the patient has indicated that the vibratory force once the amplitude of onset of sensation of vibratory force is reached, at each particular frequency, and including means for recording the amplitude at said each discrete frequency at which the patient indicates the loss of feeling as to the sensed vibration.

3. A vibratory screening or diagnostic system according to claim 1 that includes means to vary the vibration frequency, where the vibration frequency is automatically varied from discrete frequency to discrete frequency over said wide range of test frequencies.

4. A vibratory screening or diagnostic system according to claim 3 in which said means to vary the vibration frequency is operable to vary the frequency over a wide range that is between eight hertz and 800 hertz.

5. A vibratory screening or diagnostic system according to claim 4 that includes a computer connected to said means for controlling said vibratory force for controlling administration of vibratory forces by the probe to the patient, said computer including means for analyzing information received from the response recording device.

6. A vibratory screening or diagnostic system according to claim 5 further including additional measurement and control means including means to measure the temperature of the tip of the finger.

7. A vibratory screening or diagnostic system according to claim 6 further including a pulse wave monitor that measures time-amplitude of the patient's blood pulse and its timeamplitude waveform.

8. A system to sense a body pressure phenomenon of a patient or pressure-related disorder, that comprises:
  a vibratory stimulator means for applying vibratory force to the finger of the patient, including means for controlling said vibratory force to compensate for varying bias finger force onto the stimulator to permit application of a known vibratory force to said finger, despite said bias finger force;
  a drive mechanism means for effecting vibration of the vibratory stimulator means and for automatically for effecting discrete, but variable, vibrations at many frequencies over a wide range of frequencies and at variable amplified levels at each vibration frequency; and
  response means for enabling the patient to record the force corresponding to onset of sensing by the patient of vibrations at each discrete vibration frequency.

9. A vibratory screening or diagnostic system that comprises:
  a test surface to receive the hand of a patient, said test surface having an opening therethrough to receive the tip of a finger of the patient, the pulp of the tip of the finger extending into said opening;
  a vibratory probe operably associated with said test surface and extending into said opening to contact the fingertip, the probe including means for applying vibratory forces at a range of amplitudes and a range of frequencies to the pulp of the tip of the finger of the patient;
  a probe drive means connected to the vibratory probe for automatically effecting discrete, but variable, vibration frequency outputs from the vibratory probe to said tip of a finger over a wide range of test frequencies, the amplitude of vibration of said vibration frequency outputs at each discrete frequency being varied throughout a range of amplitudes from some low value which is increased to the onset of incipient sensed amplitude of vibration; and
  a response indicating means for enabling the patient to indicate the force corresponding to onset and loss of sensed vibration at each test frequency and further including means to sense back pressure upon the probe by the fingertip to permit compensation.

10. A vibratory screening or diagnostic system according to claim 9 in which the means to sense back pressure include a back pressure circuit that includes said probe and a coil associated wit the probe, which coil provides feedback signals to the back pressure circuit to permit compensation for the back pressure applied to the probe by said fingertip.

11. A vibratory screening or diagnostic system according to claim 9 which includes an automatic attenuator for decreasing, when activated, the intensity of vibration at said each frequency, said response, indicating device means including means for activating the automatic attenuator once said patient indicates said incipient sensed amplitude of vibration is reached and hence decrease the intensity of vibration, and for deactivating the automatic attenuator when the patient indicates the decreasing in intensity vibrations are no longer felt, and a computer means for effecting control of the system.

12. A system for diagnosing the condition of a body part of a patient, that comprises:
  means for applying mechanical vibrations to the body part of said patient at discrete frequencies over a range of frequencies, and for compensating for varying force by said patient to said means for applying, thereby producing mechanical vibrations of equal vibration amplitude at each discrete frequency of the range of frequencies;
  means for increasing the amplitude of vibration at each discrete frequency, of the range of frequencies, from some value below a threshold of sensing by the patient to a higher level at which the vibration is sensed by the patient; and
  means operable by said patient for noting the onset of detection of the vibration by the patient at some level of vibration as the amplitude of vibration is increased.

13. A system to effect, vibratory diagnosis of a patient to measure sensory disturbances of the patient, that comprises:
  vibratory probe means for applying a known and compensated vibratory force to a body portion of the patient, compensation being with respect to vibrations of the amplitude of the probe means to compensate for bias forces applied to the probe means by the body portion and either above or below some expected or average force by the patient;
  probe drive means connected to said vibratory probe means for energizing the vibratory probe means and for varying the frequency of vibration of the vibratory probe means over a wide range of frequencies and at various vibratory ampitude levels at each vibration frequency from a low amplitude of vibration of the vibratory probe means to a high amplitude of vibration of the vibratory probe means; and means for inputting a signal from the patient to the system indicating the onset of sensing by the patient of the vibratory force with increasing amplitude of vibration of the vibratory probe means at said each vibration frequency.

14. A vibratory stimulation system usable for diagnosis or screening of a physical condition comprising:
a test platform for receiving a body part of a patient,
a vibratory probe means mounted in the proximity of said test platform for applying a vibratory stimulus to a portion of said body part when received by said platform,
a computer means for providing control signals to said vibratory stimulation system according to a predetermined sequence,
driving means responsive to said computer means for driving said vibratory probe to provide vibration frequency outputs of said vibratory probe at a plurality of frequencies and at predetermined amplitudes,
means, operable by said patient, for indicating sensation of said vibratory stimulus by said patient, and
means for sensing a force applied to said portion of said body part at said predetermined amplitude by said vibratory probe in response to said driving means,
said computer means including means for correlating said force applied to said body part, said predetermined amplitudes and said indicating of sensation of said vibratory stimulus and outputting data regarding said sensation at said force corresponding to said predetermined amplitudes at each of said plurality of frequencies.

15. A vibratory stimulation system as claimed in claim 14, wherein said means for correlating comprises:
means for varying said predetermined amplitudes to regulate said force at each of said plurality of frequencies.

* * * * *